US008151796B2

(12) United States Patent
McDonald et al.

(10) Patent No.: US 8,151,796 B2

(45) Date of Patent: Apr. 10, 2012

(54) INFLATABLE HARNESS CREW MASK

(75) Inventors: Thomas K. McDonald, Overland Park, KS (US); Bryan N. Rogers, Liberty, MO (US); Kirsten Frogley, Shawnee, KS (US); Mike W. Veach, Platte City, MO (US); Keith R. DeBald, Gardner, KS (US)

(73) Assignee: BE Intellectual Property, Inc., Lenexa, KS (US)

( * ) Notice: Subject to any disclaimer, the term of this patent is extended or adjusted under 35 U.S.C. 154(b) by 1070 days.

(21) Appl. No.: 12/026,027

(22) Filed: Feb. 5, 2008

(65) Prior Publication Data

US 2008/0236586 A1 Oct. 2, 2008

Related U.S. Application Data

(60) Provisional application No. 60/899,434, filed on Feb. 5, 2007.

(51) Int. Cl.
*A61M 11/00* (2006.01)

(52) U.S. Cl. ......... 128/205.24; 128/201.24; 128/206.24; 2/6.1

(58) Field of Classification Search ............ 128/201.22–201.24, 206.26, 205.25, 207.11, 206.24, 206.27, 128/206.21; 2/9, 6.1, 6.2, 413, 422, 424, 2/410, 411, 416, 417, 421
See application file for complete search history.

(56) References Cited

U.S. PATENT DOCUMENTS

| | | | | |
|---|---|---|---|---|
| 3,018,776 | A | 1/1962 | Saitta et al. | |
| 3,599,636 | A | 8/1971 | Gutman et al. | |
| 4,157,090 | A | 6/1979 | Phillips | |
| 4,437,462 | A * | 3/1984 | Piljay et al. | 128/207.11 |
| 4,494,538 | A | 1/1985 | Ansite | |
| 4,664,108 | A | 5/1987 | Ansite | |
| 4,915,106 | A | 4/1990 | Aulgur et al. | |
| 5,036,846 | A | 8/1991 | Aulgur et al. | |
| 5,623,923 | A | 4/1997 | Bertheau et al. | |
| 5,664,566 | A | 9/1997 | McDonald et al. | |
| 5,690,102 | A | 11/1997 | Bertheau et al. | |
| 5,941,245 | A | 8/1999 | Hannah et al. | |
| 6,039,045 | A | 3/2000 | Bertheau et al. | |
| 6,843,388 | B1 | 1/2005 | Hollars | |
| 7,278,421 | B2 * | 10/2007 | Hannah et al. | 128/201.29 |
| 2004/0244801 | A1 | 12/2004 | Hannah et al. | |

FOREIGN PATENT DOCUMENTS

WO 2008017630 A1 2/2008

* cited by examiner

*Primary Examiner* — Steven Douglas
(74) *Attorney, Agent, or Firm* — Fulwider Patton LLP

(57) ABSTRACT

The inflatable harness crew mask includes an inflatable harness with a compressed gas supply system connected to the inflatable harness independent of oxygen supplied to the mask from an oxygen regulator. The mask includes a valve connector with an exhalation and inhalation valve and an inflation valve connected to a pressurized gas inflation supply assembly including a container portion for a compressed gas cartridge, and a regulator portion connected to provide pressurized gas from the cartridge to an inflation gas supply tube connected to the inflation valve, which is manually operable by the user.

18 Claims, 8 Drawing Sheets

FIG. 9
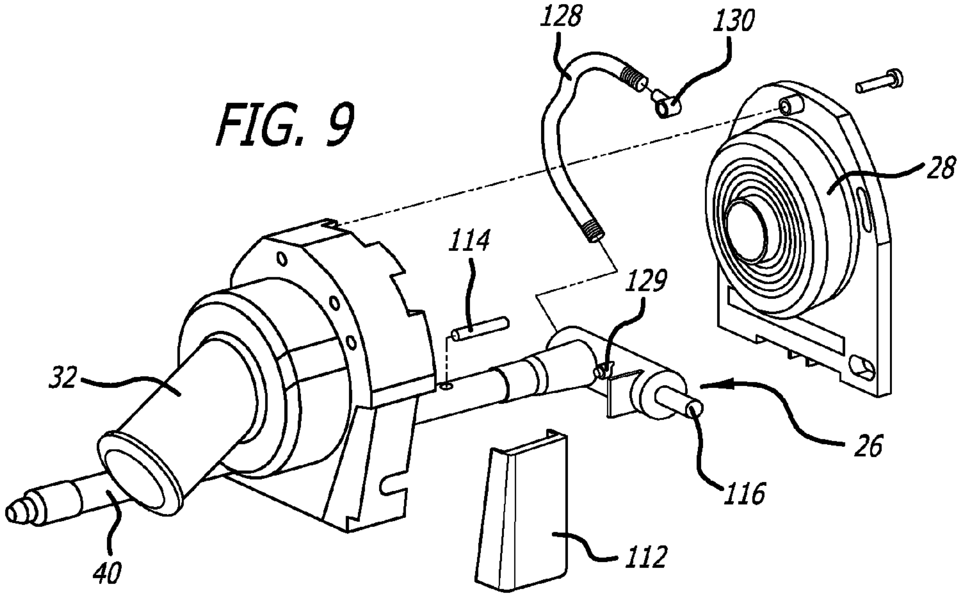
FIG. 10
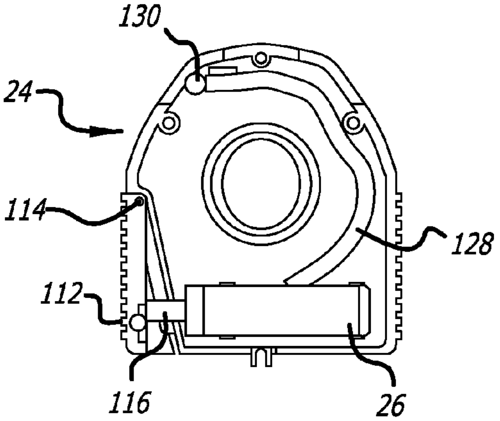
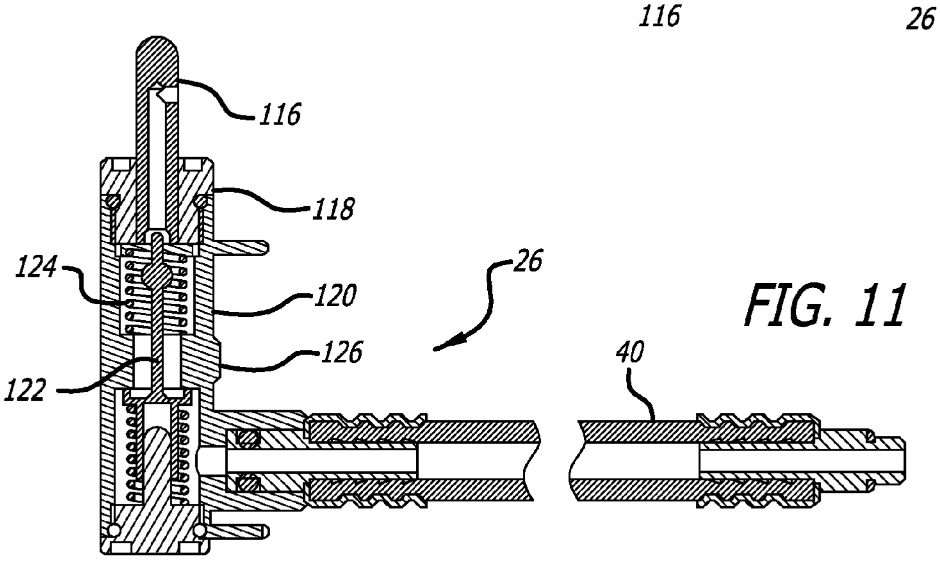
FIG. 11

INFLATABLE HARNESS CREW MASK

CROSS-REFERENCES TO RELATED APPLICATIONS

This application is based upon provisional Application No. 60/899,434, filed 5 Feb. 2007.

BACKGROUND OF THE INVENTION

This invention relates to crew masks to be used in large aircraft for crew safety in the event of decompression of the cabin. More particularly, the invention relates to the inflatable harness used to secure such a mask in place for use.

A commonly used type of crew mask includes an inflatable head harness with inflatable elastic tubes that are inflated prior to placement of the harness over the head of the user and that are then deflated to grip the user's head. A valve is connected to the tubes to control inflation by the pressurized oxygen supply of a regulator on the respiratory mask.

Another similar type of oxygen supply system includes an oxygen supply with a face mask and an inflatable head harness. A plurality of chemical oxygen generators provide pressurized oxygen to a reservoir to inflate the pneumatic head harness and provide an initial breathing supply during the startup of the chemical oxygen generators.

Aircraft crew masks with inflatable harnesses are currently limited to designs that use high pressure oxygen and regulators mounted at the mask. The high pressure oxygen supply for the regulator is also used for inflating the harness. However, longstanding designs for military oxygen masks have mounted the high pressure oxygen supply and the oxygen regulator in the aircraft panel, providing lower pressure breathable oxygen to the masks, so that no high pressure oxygen gas is available at the mask to inflate a harness. Current military masks are limited to older "hard" head harnesses requiring adjustment to fit, or are supported by a flight helmet. Inflatable harness masks are preferred because they fit a range of personnel head sizes without requiring pre-adjustment or custom sized designs required of the older hard head harnesses. Thus, it would be desirable to provide an inflatable harness crew mask adapted to allow rapid inflation of the harness, to allow adaptation of the older style military mask designs to gain the benefit of automatic adjustability of modern inflatable harnesses. The current invention solves these and other problems.

SUMMARY OF THE INVENTION

Briefly, and in general terms, the present invention provides for an inflatable harness crew mask with an inflatable harness utilizing a separate pressurized gas inflation supply assembly, independent from an oxygen supply system, to supply pressurized gas to inflate the inflatable harness, allowing the inflatable harness crew mask to be connected to an oxygen supply regulator mounted in an aircraft panel and providing lower pressure breathable oxygen to the mask, and allowing the inflatable harness to be inflated, independently of oxygen supplied from the oxygen supply regulator, to fit over the head of a user without requiring pre-adjustment or custom fitting.

The present invention accordingly provides for an inflatable harness crew mask, including a mask portion including a face seal molding formed to fit around the periphery of the face of the wearer, and an inflatable harness including at least one inflatable tube connected to the face seal molding. An inflation valve is connected in fluid communication with the inflatable harness to control inflation of the harness, and a pressurized gas inflation supply assembly is configured to supply pressurized gas to the inflation valve to inflate the inflatable harness. In a presently preferred aspect, the mask portion includes a valve connector housing, and an exhalation and inhalation valve is disposed in the valve connector housing and connected in fluid communication with the mask portion. The exhalation and inhalation valve includes an inlet configured to be connected to a source of oxygen for providing breathable oxygen to the mask portion. In another presently preferred aspect, the inflation valve is also disposed in the valve connector housing.

The inflation valve of the inflatable harness crew mask includes a housing having an inlet port and an outlet port, and an inflation valve poppet slidably disposed in the inflation valve housing, with a plunger pin slidably disposed in a first end of inflation valve housing and abutting the inflation valve poppet. The plunger pin is biased to a closed position, and a gas release button is pivotally connected to the valve connector housing and disposed adjacent to the plunger pin, allowing a user to manually press the gas release button to open the inflation valve poppet, and to in turn release pressured gas through the inflation valve outlet port. In another aspect, the inflation valve includes a pressure adjusting assembly. The inflatable harness may include first and second inflatable tubes configured to fit over the head of a user, may include one or more connecting straps connected between the first and second inflatable tubes, and the one or more connecting straps may be adjustable.

In another presently preferred aspect, the pressurized gas inflation supply assembly includes a pressurized gas inflation supply cylinder having a container portion with an interior chamber for removably receiving a main body portion of a compressed gas cartridge, and a regulator portion configured to removably receive a neck portion of the compressed gas cartridge at a first end of the regulator portion. The second end of the regulator portion includes a gas outlet port connected to the outlet end of the piercing lance member, and the gas outlet port of the regulator is connected to an inflation gas supply tube. The first end of the regulator portion is removably connectable to the container portion, and includes an interior plenum configured to removably receive the neck portion of a compressed gas cartridge. In another presently preferred aspect, the compressed gas cartridge is configured to provide sufficient compressed gas for multiple inflations of the inflatable harness, and the compressed gas cartridge is a compressed carbon dioxide gas cartridge.

The gas outlet port at the second end of the regulator portion of the pressurized gas inflation supply cylinder is connected to the inflation valve by the inflation gas supply tube. The first end of the regulator portion also preferably includes a piercing lance member having a conical pierce point inlet configured to pierce a septum of the neck portion of the compressed gas cartridge, and the piercing lance member includes an interior aperture configured to allow gas flow extending therethrough from the gas cartridge to an outlet end of the piercing lance member.

In another aspect, the regulator portion preferably includes a regulator valve adjacent to the outlet end of the piercing lance member. The regulator valve includes a regulator valve chamber, and a ball member disposed in the regulator valve chamber. The second end of the regulator valve may also include a gas pressure adjusting assembly configured to regulate the pressure of the gas released from the compressed gas cartridge to a desired lower harness inflation tube pressure. A pressure charge indicator assembly may also be mounted in fluid communication with the regulator valve chamber.

Other features and advantages of the present invention will become more apparent from the following detailed description of the preferred embodiments in conjunction with the accompanying drawings, which illustrate, by way of example, the operation of the invention.

BRIEF DESCRIPTION OF THE DRAWINGS

FIG. 9 is an exploded perspective view of the valve connector and inflation valve of the inflatable harness crew mask of FIG. 1.

FIG. 10 is a cross-sectional view of the valve connector of FIG. 1.

FIG. 11 is a cross-sectional view of the inflation valve of the inflatable harness crew mask of FIG. 1.

DETAILED DESCRIPTION OF THE PREFERRED EMBODIMENTS

While crew masks with an inflatable head harness are useful in placing a harness of a mask over the head of the user, pressurized oxygen that is commonly used to inflate such an inflatable harness is not available in some aircraft, such as military aircraft, so that a method and system for inflating an inflatable harness of a crew mask is needed that can be used in such aircraft in which a source of pressurized oxygen is not available for inflation of a crew mask head harness.

Figure 13:
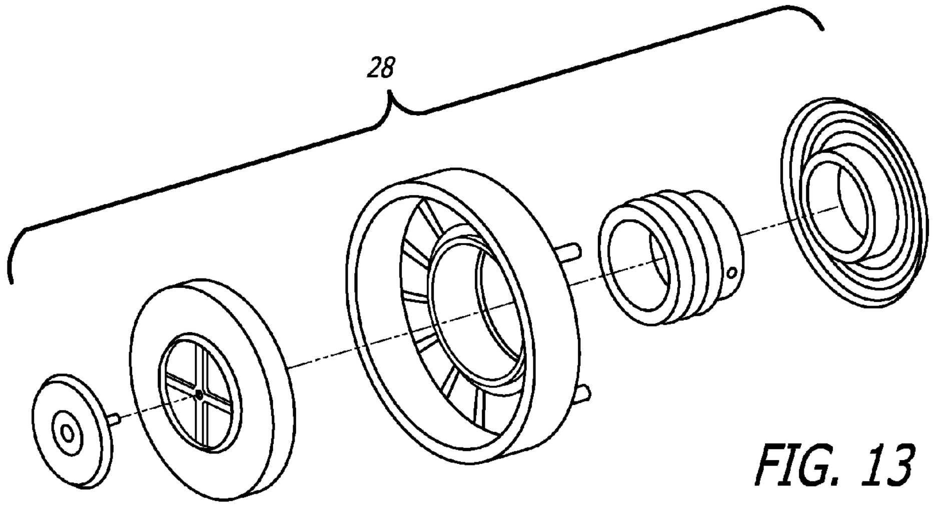
FIG. 13 is an exploded perspective view of the exhalation and inhalation valve of the valve connector.

Referring to the drawings, which are provided by way of illustration and not by way of limitation, the invention is embodied in an inflatable harness crew mask 10, having a mask portion 11 typically including a clear flexible lens 12 mounted in an elastomeric face seal molding 14 formed to fit around the periphery of the face of the wearer, as is illustrated in FIGS. 1-4. The inflatable harness crew mask includes an inflatable harness 16 including individual inflatable tubes 18*a*, 18*b* configured to fit over the head of a user is attached to the elastomeric face seal molding. Connecting straps 20 and 22 may also be connected at their extremities between the inflatable tubes and may also be adjustable for the size of the mask and comfort of the user once the harness is fitted over the user's head. The lower forward portion of the elastomeric face seal molding includes a valve connector housing 24 including an inflation valve 26, shown in FIGS. 9-12, for controlling inflation of the harness, and an inhalation/exhalation valve 28, shown in FIGS. 9 and 13.

Figure 1:
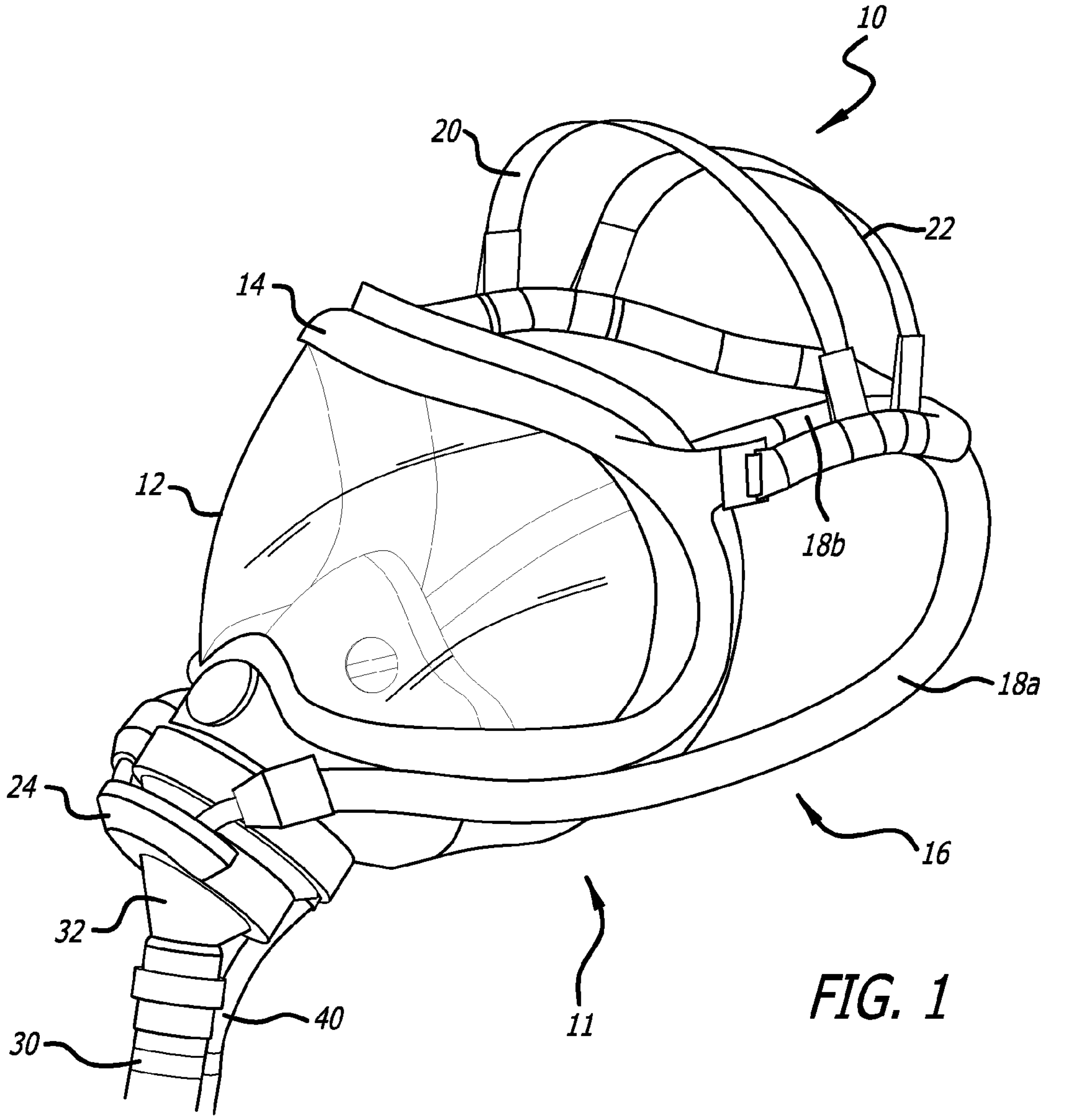
FIG. 1 is a front perspective view of an inflatable harness crew mask according to the present invention.
Figure 2:
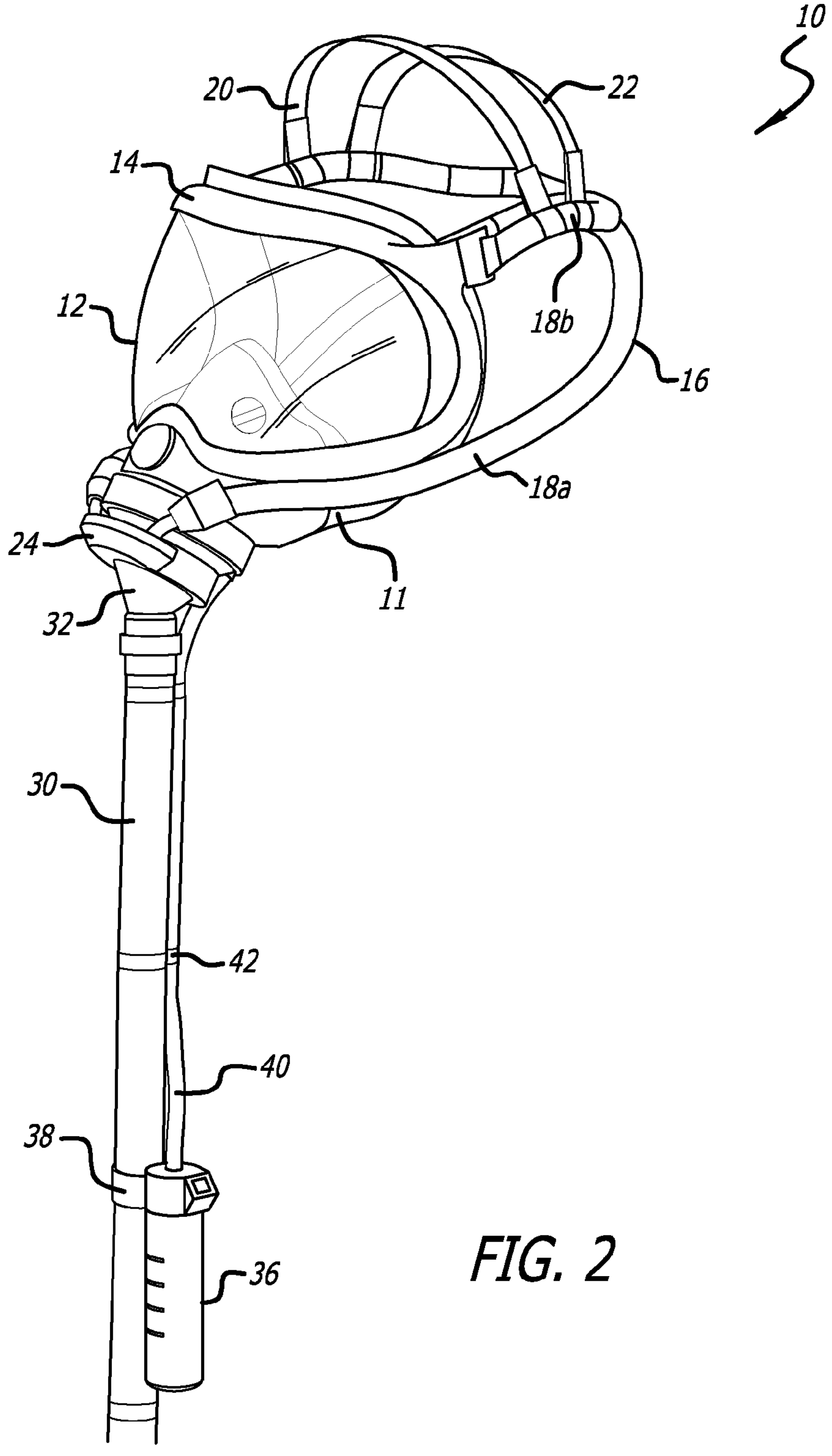
FIG. 2 is a left side front perspective view of an inflatable harness crew mask of FIG. 1, showing the gas cartridge inflator for the inflatable harness of the crew mask.
Figure 4:
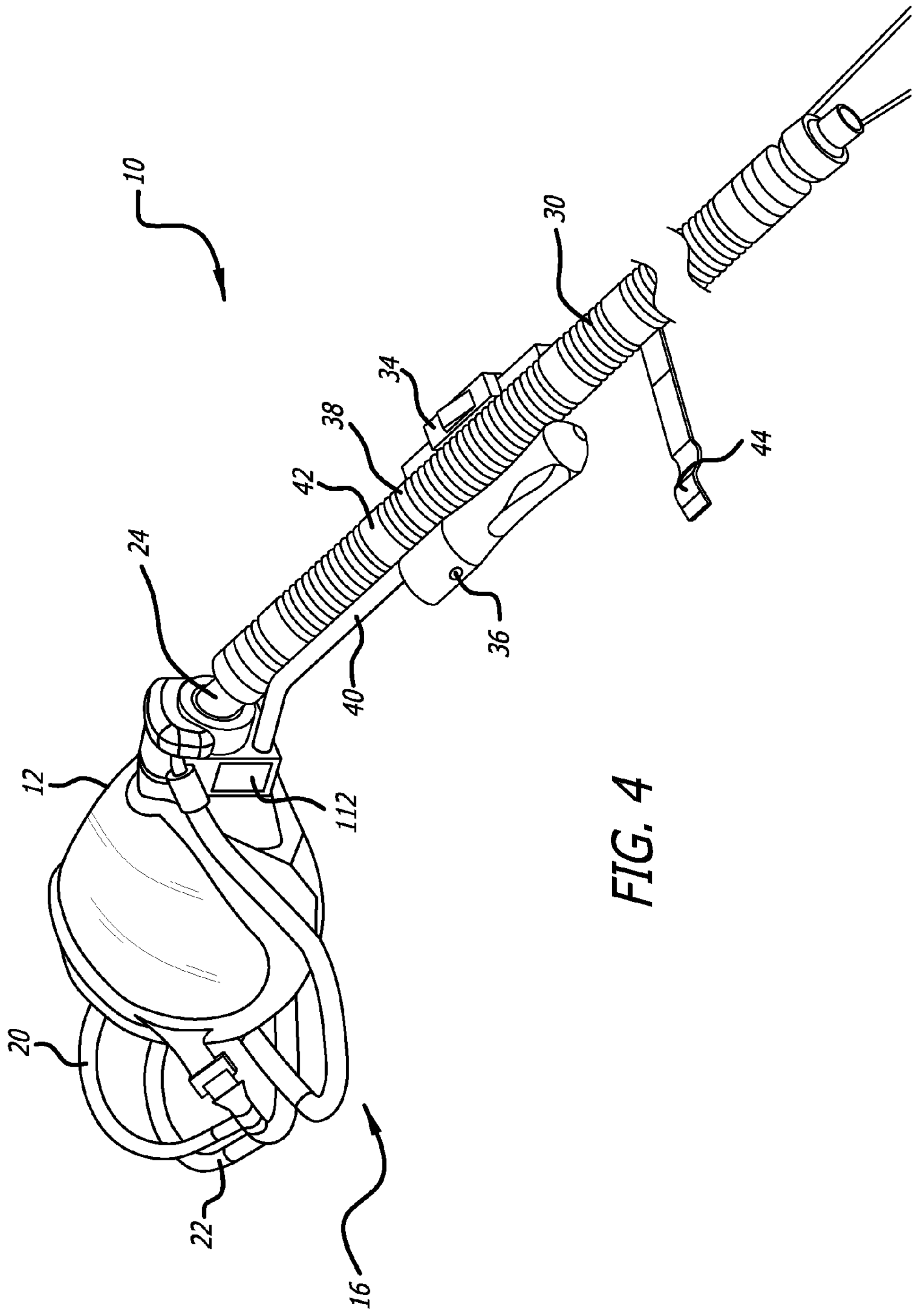
FIG. 4 is a right side front perspective view of an inflatable harness crew mask of FIG. 1, showing a variation of the gas cartridge inflator for the inflatable harness of the crew mask.

Referring to FIGS. 1, 2 and 4, an oxygen supply for the inflatable harness crew mask is provided by an oxygen supply hose or tube 30 connected at one end to an inlet 32 of the valve connector housing, and connected at the opposing end of the oxygen supply hose to an oxygen supply regulator in an aircraft (not shown). The flow of oxygen from the inlet of the valve connector housing to the mask is controlled by the inhalation/exhalation valve which is connected to the interior of the mask. As is illustrated in FIG. 4, in order to facilitate communication, the mask may also incorporate a microphone (not shown) having a "press to talk" control 34 mounted on the oxygen supply hose.

As is shown in FIGS. 2-6, a small compressed gas inflation supply cylinder 36 that provides enough gas for multiple inflations of the harness is typically also mounted to the oxygen supply hose by a clamp or clip 38, for supplying pressurized gas, such as carbon dioxide gas, via an inflation gas supply tube 40, typically also mounted to the oxygen supply hose by a clamp or clip 42, to the inflation valve connector. A clothing clip 44 connected to the oxygen supply hose may also be provided for removably attaching the oxygen supply hose to the user's clothing.

Figure 3:
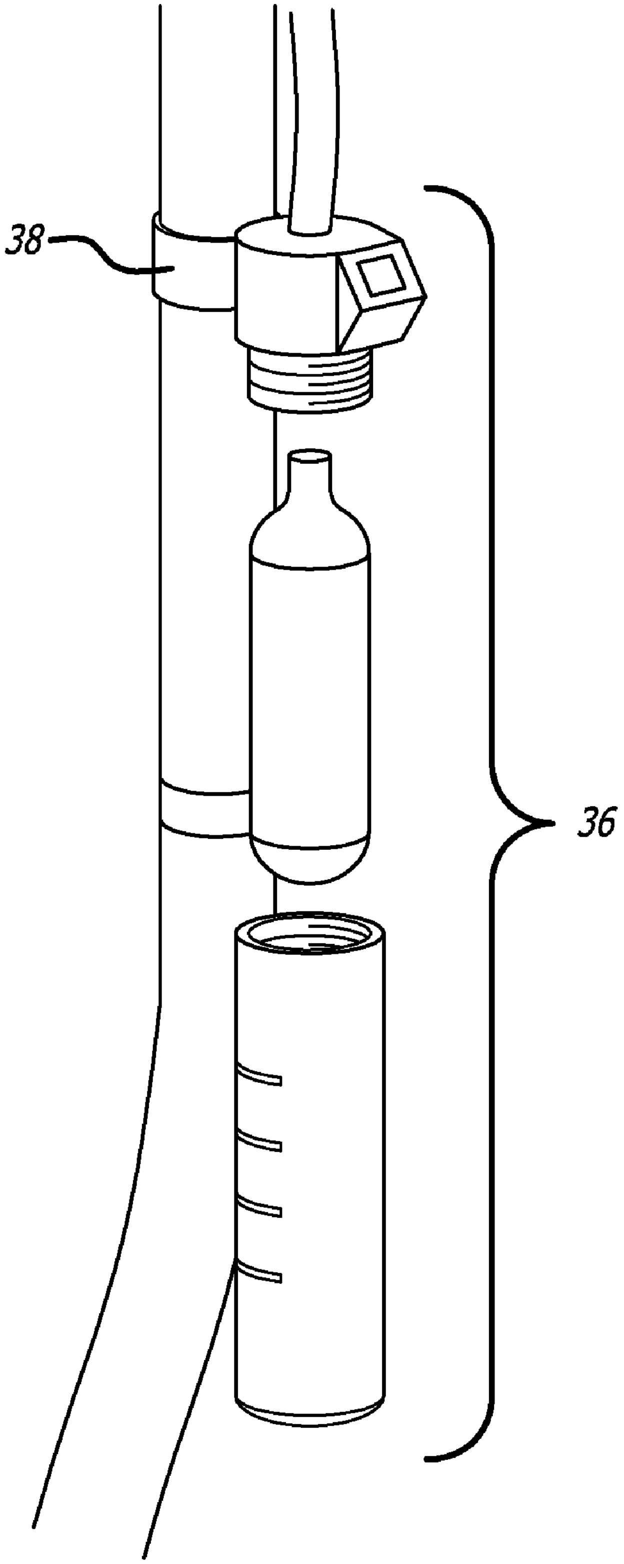
FIG. 3 is an exploded view of the gas cartridge inflator for the inflatable harness of the crew mask of FIG. 2.

Referring to FIGS. 5-8, the gas inflation supply cylinder includes a container portion 46 having an interior chamber 48 for removably receiving a compressed gas cartridge 50, such as a standard $CO_2$ compressed gas cartridge pressurized over 800 psig. The neck 52 of the compressed gas cartridge is removably received in an interior plenum 54 of a regulator portion 56 of the gas inflation supply cylinder that is typically threadably connectable to the container portion of the gas inflation supply cylinder as shown in FIGS. 1-3. The neck of the compressed gas cartridge may be threaded or non-threaded, and includes a septum (not shown) that may be pierced to release pressurized gas in the cartridge.

Figure 5:
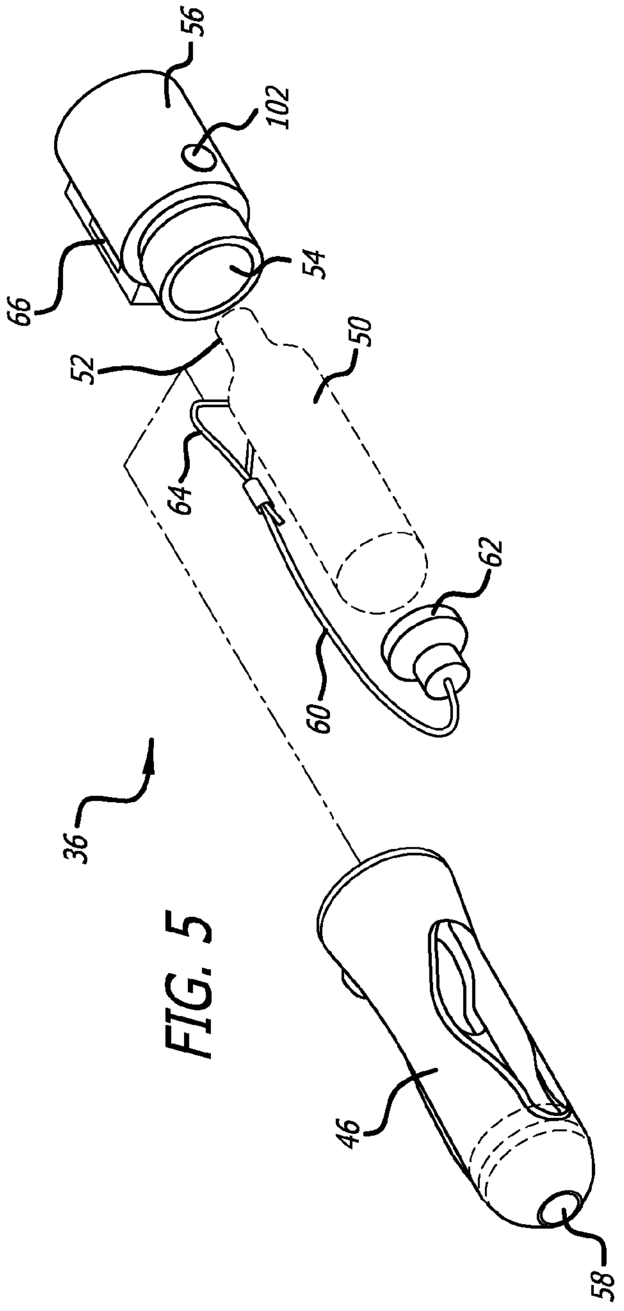
FIG. 5 is an exploded perspective view of the gas cartridge inflator of FIG. 4.
Figure 6:
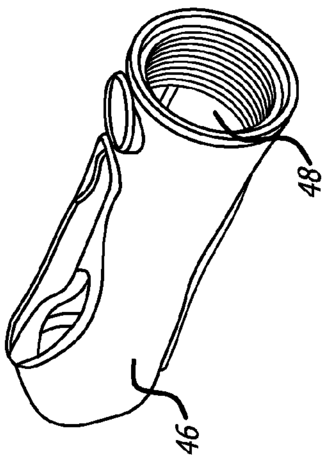
FIG. 6 is a front perspective view of the gas cartridge container portion of the gas cartridge inflator of FIG. 4.

Referring to FIG. 5, the container portion may include an aperture 58 allowing a lanyard 60 to be threaded through the aperture, with the cup member retained within the interior chamber of the container portion, with the other end 64 of the lanyard threaded through a slot 66 of the regulator portion, for loosely keeping the container and regulator portions connected when they are disassembled for insertion or removal of a gas cartridge.

Figure 7:
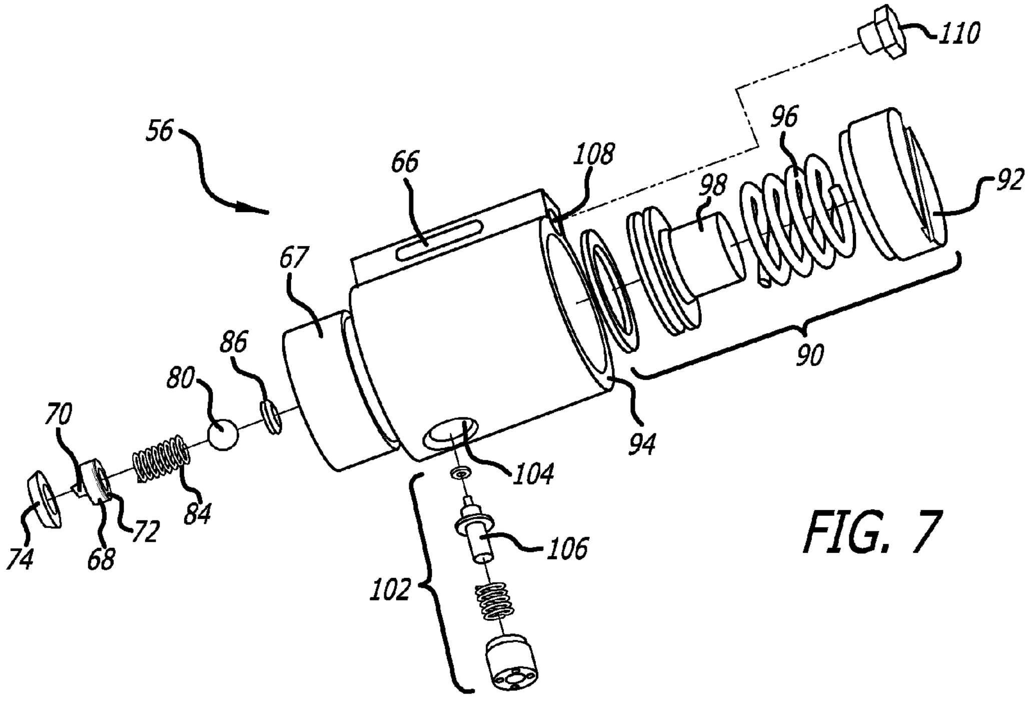
FIG. 7 is an exploded perspective view of the regulator portion of the gas cartridge inflator of FIG. 4.
Figure 8:
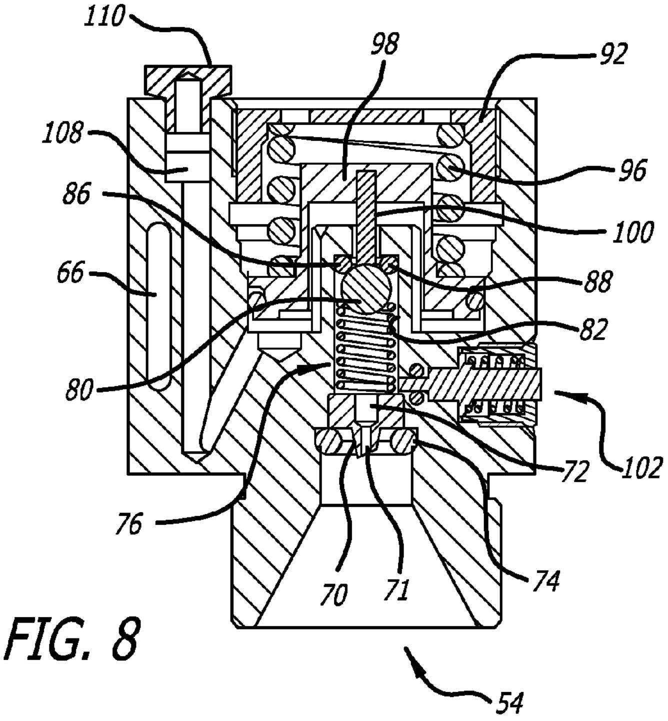
FIG. 8 is a cross-sectional view of the regulator portion of the gas cartridge inflator of FIG. 4.
Figure 12:
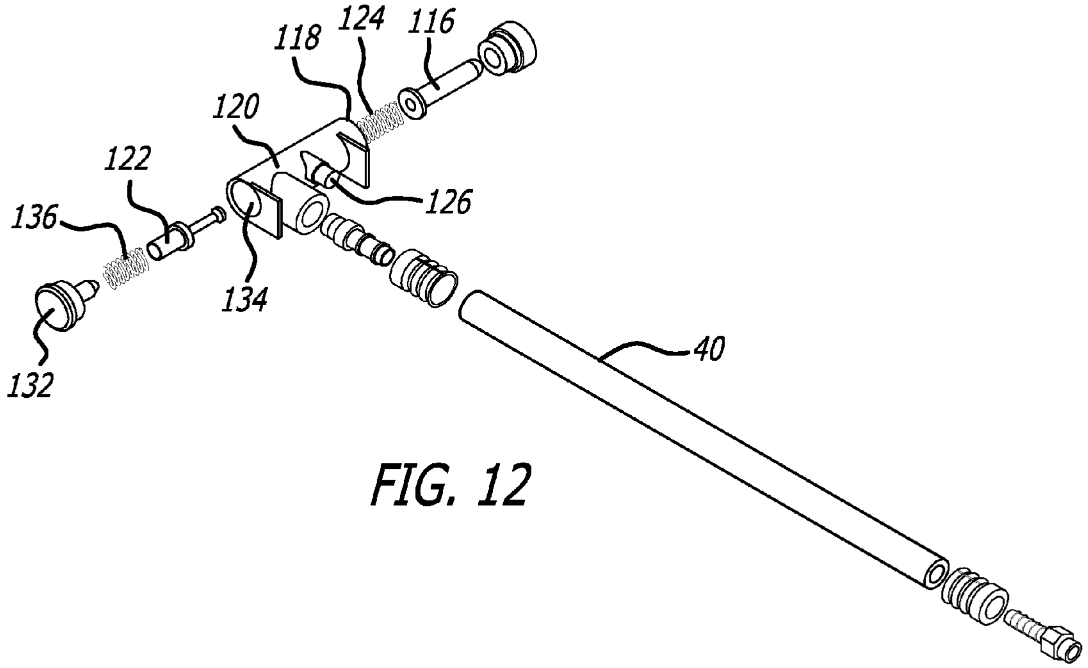
FIG. 12 is an exploded perspective view of the inflation valve of the inflatable harness crew mask of FIG. 1.

Referring to FIGS. 7 and 8, mounted at a first end 67 of the regulator portion is a piercing lance member 68 having a conical pierce point inlet 70 for piercing the neck of the compressed gas cartridge, and having an interior aperture 71 to allow gas flow extending therethrough from the gas cartridge to an outlet end 72 of the piercing lance member, with a ring seal 74 disposed around the conical pierce point for sealing contact with the non-threaded neck of the compressed gas cartridge.

The regulator includes a ball valve 76 adjacent to the outlet end of the piercing lance member, including a ball member 80 disposed in the ball valve chamber 82, with a ball valve closing compression spring 84 disposed between the ball member and the outlet end of the piercing lance member and configured to bias the ball member against a ring seal 86 disposed between the ball member and the valve seat 88, to thereby bias the ball valve to be closed, at the upper end of the ball valve chamber. The regulator also includes a gas pressure adjusting assembly 90 mounted in the regulator for regulating the pressure of the gas released from the gas cartridge to a desired lower harness inflation tube pressure. The gas pressure adjusting assembly includes a pressure adjusting screw 92 threadably mounted in the second end 94 of the regulator. A main compression spring 96 is disposed between the pressure adjusting screw and a compression plate member 98, and a pin 100 is disposed between the ball member and the compression plate member to transfer pressure from the pressure adjusting screw through its associated compression spring to bias the ball member open against the valve closing pressure of the ball valve closing compression spring, for controlling gas released from the gas cartridge to a desired lower harness inflation tube pressure, such as approximately 70 psig, for example. The compression of the main spring determines the regulated pressure.

A pressure charge indicator assembly 102 is preferably mounted in an aperture 104 at the side of the regulator and connected with the ball valve chamber, including an indicator poppet or button 106 that pops out when a new cylinder is engaged and stays out until the pressure falls below a threshold pressure, such as approximately 100 psig for example. This indication is used to alert the user that there is a sufficient gas pressure charge in the gas cartridge of the cylinder for at least one more inflation of the inflatable harness left in the cylinder if the poppet is out or up.

The inflation gas supply tube is connected to a gas outlet port 108 of the regulator that is connected in fluid communication with the interior ball valve chamber for supplying pressurized gas to the inflatable harness. As is illustrated in FIG. 7, the gas outlet port of the regulator may be temporarily sealed with a hex plug 110 if the inflation gas supply tube is disconnected from the regulator, such as for replacing the compressed gas inflation supply cylinder, such as with one of a different capacity, for example.

Referring to FIGS. 9-12, the inflation valve controls the supply of pressurized gas through the inflation valve to the harness, and includes a gas release button 112 pivotally connected by hinge pin 114 to the valve connector housing and disposed adjacent to a plunger pin 116 slidably disposed in the a first end 118 of a generally tubular inflation valve housing 120 and abutting the inflation valve poppet 122 disposed in the housing, with the plunger pin biased to a closed position by the main plunger compression spring 124, allowing a user to press against the gas release button to open the inflation valve poppet against the force of the main plunger compression spring to release pressured gas through the inflation valve outlet port 126.

A gas connector tubing 128 is connected to the inflation valve outlet port to conduct the pressurized gas to an outlet fitting connector 130 which is in turn connected to the inflatable tubes of the inflatable harness. A pressure adjusting screw 132 is threadably mounted in the second end 134 of the inflation valve housing. A main compression spring 136 is disposed between the pressure adjusting screw and the base of the inflation valve poppet to bias the inflation valve poppet closed.

Prototype Testing:

A functional unit of the invention was mocked up using a commercially available carbon dioxide, 16-gram inflator for bicycle tires. The unit was connected to the harness supply valve of an existing inflatable harness full-face crew mask. The results shown in the table below were observed after testing three cartridges at an ambient temperature of 70° F. for 10 to 12 inflations average.

| Crew Mask Harness | | | |
|---|---|---|---|
| | Length (in) | I.D. (0 psi) | I.D. (70 psi) |
| Harness Tube A | 18.5 | 0.375 | 0.437 |
| Harness Tube B | 17.75 | 0.375 | 0.437 |
| Volume of Harness | Cubic Inches | 4 | 5.43 |
| Volume of Gas | Liter | 0.06 | 0.51 |
| | Cubic Inches | 4 | 31.3 |

-continued

| Crew Mask Harness | | | |
|---|---|---|---|
| Harness Fill Rate | Volume (l) | 0.51 | |
| | Time (min)* | 0.016 | |
| | Flow Rate (LPM) | 31.875 | |
| Carbon Dioxide | Liquid to Gas | 1 gram = 30.5 cu in | STPD |
| | Specific Gravity | 1.522 | |
| | Molecular Weight | 44 | |
| | Gas Density | 1.85 | kg/m3 |
| | Cartridge Size (g) | Temp (F.) | Harness Cycles |
| Harness filling | 16 | 0 | 15 |
| | 16 | 70 | 18 |
| | 16 | 120 | 20 |
| 800 psi | Based on liquid to gas conversion @ 70 F. typical is 9 to 10 liters of gas @ storage pressure | | |

*Maximum allowable harness inflation time

From the foregoing, it thus can be seen that the invention uses a compressed gas cylinder mounted on the crew mask and connected to the inflatable harness for supplying pressurized gas to the inflatable harness independent of breathable oxygen supplied to the crew mask. Specifically, the invention uses a small compressed gas cylinder and regulator which are mounted on an aircraft crew member's oxygen mask, thus causing the mask harness to inflate and be donned quickly over one's head. The cylinder provides enough gas for multiple inflations of the harness and allows older military masks which interface to panel mounted regulators to be reconfigured to have the newer preferred inflatable harness. The invention provides economically added and simply constructed means of adapting modern inflatable harness technology to older crew masks, thus avoiding the cost and logistic complexity, particularly for military aircraft, of replacing a large investment in masks and equipment.

It will be apparent from the foregoing that while particular forms of the invention have been illustrated and described, various modifications can be made without departing from the spirit and scope of the invention. Accordingly, it is not intended that the invention be limited, except as by the appended claims.

The invention claimed is:

1. An inflatable harness crew mask, comprising:

a mask portion including a face seal molding formed to fit around the periphery of the face of the wearer;

an inflatable harness including at least one inflatable tube connected to the face seal molding;

an inflation valve connected in fluid communication to said inflatable harness and configured to control inflation of the harness, wherein said inflation valve comprises an inflation valve housing having a first end and a second end, an inlet port and an outlet port, an inflation valve poppet slidably disposed in said inflation valve housing, a plunger pin slidably disposed in the first end of inflation valve housing and abutting the inflation valve poppet, said plunger pin being biased to a closed position, and a gas release button pivotally connected to the valve connector housing and disposed adjacent to the plunger pin allowing a user to press against the gas release button to open the inflation valve poppet to release pressured gas through the inflation valve outlet port; and a pressurized gas inflation supply assembly configured to supply pressurized gas to the inflation valve to inflate the inflatable harness.

2. The inflatable harness crew mask of claim 1, wherein said mask portion includes a valve connector housing, and further comprising an exhalation and inhalation valve disposed in said valve connector housing and connected in fluid communication with the mask portion, said exhalation and inhalation valve having an inlet configured to be connected to a source of oxygen for providing breathable oxygen to said mask portion.

3. The inflatable harness crew mask of claim 2, wherein said inflation valve is disposed in said valve connector housing.

4. The inflatable harness crew mask of claim 1, wherein said inflation valve comprises a pressure adjusting assembly including a pressure adjusting screw threadably mounted in the second end of the inflation valve housing, a compression plate member disposed in the inflation valve housing and abutting a base of the inflation valve poppet to bias the inflation valve poppet closed, and a main compression spring disposed between the pressure adjusting screw and the compression plate member.

5. The inflatable harness crew mask of claim 1, wherein said inflatable harness comprises first and second inflatable tubes configured to fit over the head of a user.

6. The inflatable harness crew mask of claim 5, wherein said inflatable harness comprises at least one connecting strap connected between said first and second inflatable tubes.

7. The inflatable harness crew mask of claim 6, wherein said at least one connecting strap is adjustable.

8. An inflatable harness crew mask, comprising:

a mask portion including a face seal molding formed to fit around the periphery of the face of the wearer;

an inflatable harness including at least one inflatable tube connected to the face seal molding;

an inflation valve connected in fluid communication to said inflatable harness and configured to control inflation of the harness; and a pressurized gas inflation supply assembly configured to supply pressurized gas to the inflation valve to inflate the inflatable harness, wherein said pressurized gas inflation supply assembly includes a pressurized gas inflation supply cylinder including a container portion having an interior chamber for removably receiving a main body portion of a compressed gas cartridge, and a regulator portion, said regulator portion having a first end and a second end, said first end of said regulator portion being removably connectable to said container portion, and said first end of said regulator portion having an interior plenum configured to removably receive a neck portion of a compressed gas cartridge.

9. The inflatable harness crew mask of claim 8, wherein said compressed gas cartridge comprises a carbon dioxide compressed gas cartridge.

10. The inflatable harness crew mask of claim 8, wherein said compressed gas cartridge is configured to provide sufficient compressed gas for multiple inflations of the inflatable harness.

11. The inflatable harness crew mask of claim 8, wherein said second end of said regulator portion of said pressurized gas inflation supply cylinder is connected to said inflation valve by an inflation gas supply tube.

12. The inflatable harness crew mask of claim 11, wherein said first end of said regulator portion comprises a piercing lance member having a conical pierce point inlet and an outlet end, said conical pierce point inlet being configured to pierce a septum of the neck portion of the compressed gas cartridge, and said piercing lance member including an interior aperture configured to allow gas flow extending therethrough from the gas cartridge to said outlet end of the piercing lance member.

13. The inflatable harness crew mask of claim 8, wherein said regulator portion comprises a regulator valve adjacent to the outlet end of the piercing lance member.

14. The inflatable harness crew mask of claim 13, wherein said regulator valve comprises a regulator valve chamber, and a ball member disposed in the regulator valve chamber.

15. The inflatable harness crew mask of claim 14, wherein said second end of the regulator comprises a gas pressure adjusting assembly configured to regulate the pressure of the gas released from the compressed gas cartridge to a desired lower harness inflation tube pressure.

16. The inflatable harness crew mask of claim 15, wherein said gas pressure adjusting assembly comprises a pressure adjusting screw threadably mounted in the second end of the regulator, a main compression spring disposed between the pressure adjusting screw and a compression plate member, and a pin disposed between the ball member and the compression plate member configured to transfer pressure from the pressure adjusting screw to bias the ball member open against the valve closing pressure of the regulator valve closing compression spring, for controlling gas released from the gas cartridge to a desired lower harness inflation tube pressure.

17. The inflatable harness crew mask of claim 12, wherein said regulator portion comprises a gas outlet port connected to said outlet end of the piercing lance member, and said gas outlet port of the regulator is connected to said inflation gas supply tube.

18. The inflatable harness crew mask of claim 14, further comprising a pressure charge indicator assembly mounted in fluid communication with said regulator valve chamber.

* * * * *